US009241862B2

(12) United States Patent
Wilkins

(10) Patent No.: US 9,241,862 B2
(45) Date of Patent: Jan. 26, 2016

(54) THERAPY APPARATUS

(75) Inventor: Larry C. Wilkins, Ft. Lauderdale, FL (US)

(73) Assignee: WILKINS IP, LLC, New Albany, IN (US)

( * ) Notice: Subject to any disclaimer, the term of this patent is extended or adjusted under 35 U.S.C. 154(b) by 2723 days.

(21) Appl. No.: 11/734,325

(22) Filed: Apr. 12, 2007

(65) Prior Publication Data

US 2008/0255479 A1 Oct. 16, 2008

(51) Int. Cl.

| | |
|---|---|
| ***A61B 5/16*** | (2006.01) |
| ***A61H 1/02*** | (2006.01) |
| ***A63B 21/00*** | (2006.01) |
| ***A63B 23/035*** | (2006.01) |
| *A63B 24/00* | (2006.01) |
| *A63B 69/00* | (2006.01) |
| *A63B 71/00* | (2006.01) |
| *A63B 71/06* | (2006.01) |

(52) U.S. Cl.

CPC ........ *A61H 1/0266* (2013.01); *A63B 21/00047* (2013.01); *A63B 23/035* (2013.01); *A61H 1/0262* (2013.01); *A61H 2201/1635* (2013.01); *A61H 2201/5048* (2013.01); *A61H 2201/5058* (2013.01); *A61H 2201/5092* (2013.01); *A61H 2201/5097* (2013.01); *A61H 2203/0406* (2013.01); *A63B 24/0075* (2013.01); *A63B 69/0053* (2013.01); *A63B 71/0009* (2013.01); *A63B 71/0622* (2013.01); *A63B 2208/0204* (2013.01)

(58) Field of Classification Search

USPC ........................................................ 463/7, 36

See application file for complete search history.

(56) References Cited

U.S. PATENT DOCUMENTS

| | | | | |
|---|---|---|---|---|
| 3,611,591 A * | 10/1971 | Light | ............................ | 434/252 |
| 5,603,617 A * | 2/1997 | Light | ............................ | 434/252 |
| 6,227,968 B1 * | 5/2001 | Suzuki et al. | ...................... | 463/7 |
| 2001/0022574 A1 * | 9/2001 | Hwang | .......................... | 345/156 |

* cited by examiner

*Primary Examiner* — Sam Yao
*Assistant Examiner* — Evan Page
(74) *Attorney, Agent, or Firm* — Finnegan, Henderson, Farabow, Garrett & Dunner, L.L.P.

(57) ABSTRACT

A machine has a platform for a standing patient to perform foot exercises specified by a set of selectors on the machine and pre-selected according to a therapy program. Different types of monitor devices viewable by the patient and an attendant, direct the patient to proceed with selected exercises. Light sources associated with the platform to illuminate portions of it, and other slight sources directed to sensors above the platform, are activated in concert, according to the directions addressed to the patient.

27 Claims, 18 Drawing Sheets

THERAPY APPARATUS

BACKGROUND

This invention relates generally to a rehabilitation therapy machine and more particularly to a machine for assisting a therapist with a patient recovering foot and toe functions.

Among the many problems that can be encountered by a person who has suffered brain injury due to a head injury or stroke or other cause, is the inability to use the feet and toes. Recovery from such problems can often necessitate close and constant attention by a therapist supervising the efforts of the patient to move the foot and/or toes during therapy sessions. Also, it is often difficult for the patient to observe and be mindful of the progress being made toward goals to be reached. Similarly, sometimes it is difficult for the therapist to observe and keep track of progress between one therapy session and another, and over a period of time. Improvement in these regards is needed.

SUMMARY

Human patient therapy apparatus has a machine providing means to support a standing patient for foot exercises, with means for a therapist to prescribe certain ones of a set of possible foot exercises, with means to direct the patient to proceed with the prescribed exercises, with means for the patient to receive the directions, and means to note patient progress.

DETAILED DESCRIPTION OF THE ILLUSTRATED EMBODIMENT

Figure 1:
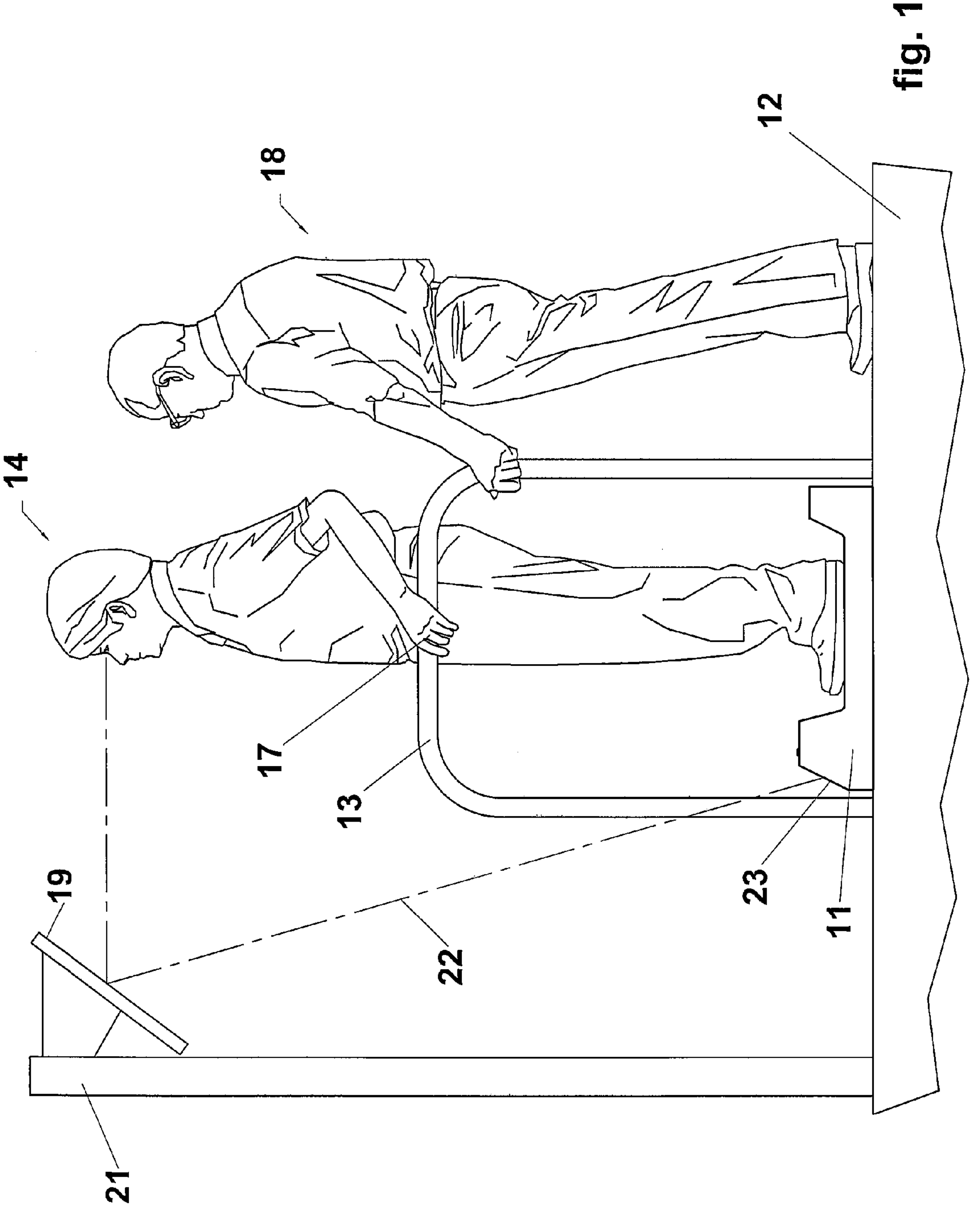
FIG. 1 is a schematic illustration of the therapy apparatus including the therapy machine and a mirror system.
Figure 2:
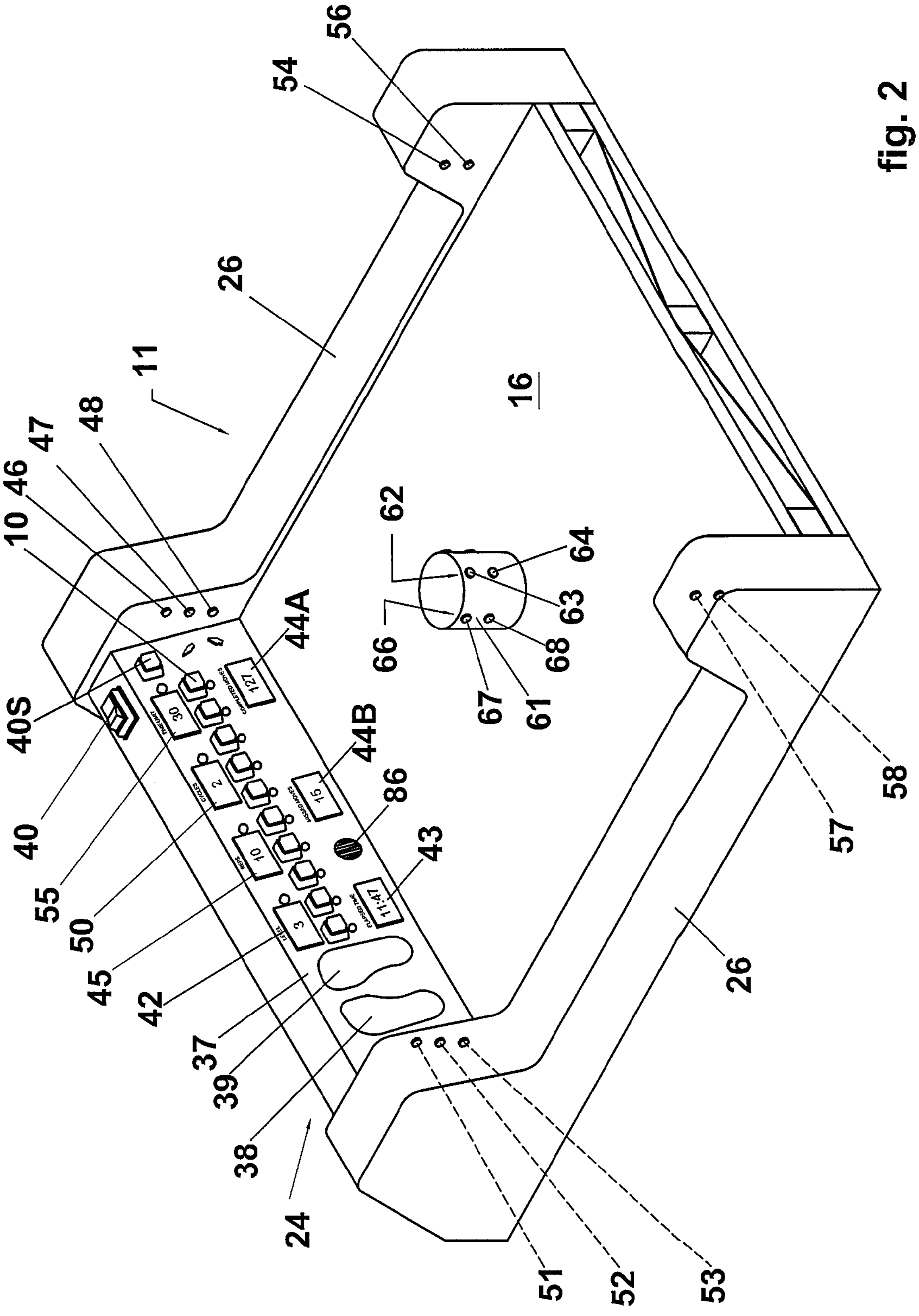
FIG. 2 is an enlarged perspective view of the therapy machine itself turned off.

Referring now to the drawings in detail and FIGS. 1 and 2 in particular, FIG. 1 shows a therapy station in which a therapy machine 11 is placed on the floor 12 between a pair (one shown) of support railings 13 mounted on the floor. The patient 14 is standing on a platform 16 of the machine and is gripping one or the other of the railings with the left hand 17 and right hand (not shown). A therapist 18 is standing on the floor 12 behind the therapy machine 11. A mirror 19 mounted on a post 21 or wall or otherwise, is tilted to provide for the patient a view along light-path 22, of the panel 23 on the front face of a control housing 24 at the front portion of the machine. The mirror is adjustable for height and angle for convenience of the patient to view the image.

Referring now particularly to FIGS. 2-7, the illustrated embodiment of the machine 11 has a frame with front and rear portions and side walls 26. It contains the platform 16, bottom panel 27, side support rails 28, center support rail 29 and reflector panel 31. All of this can be secured together by adhesives or other conventional fastening means. The platform 16 can be made of a Lexan® brand transparent material or some other material sturdy enough for the patient to stand on and yet having portions clear enough for light to pass through it. The reflector panel 31 may be made of a material with formed-in prismatic contour portions, as in vehicle reflector markers, or it can have reflector tape mounted on the top of the panel, for example. Lighting is selectively applied to the top of the reflector panel 31 below the platform by platform lighting sources. In the illustrated example, they are light-emitting diodes (LEDs) 32-36 received through holes in the support rails 28 to project light inwardly onto panel 31 as indicated by the dashed lines 36L for one quadrant of the panel 31 in FIG. 5. Light producing devices other than LEDs and arranged otherwise might also be used.

Figure 5:
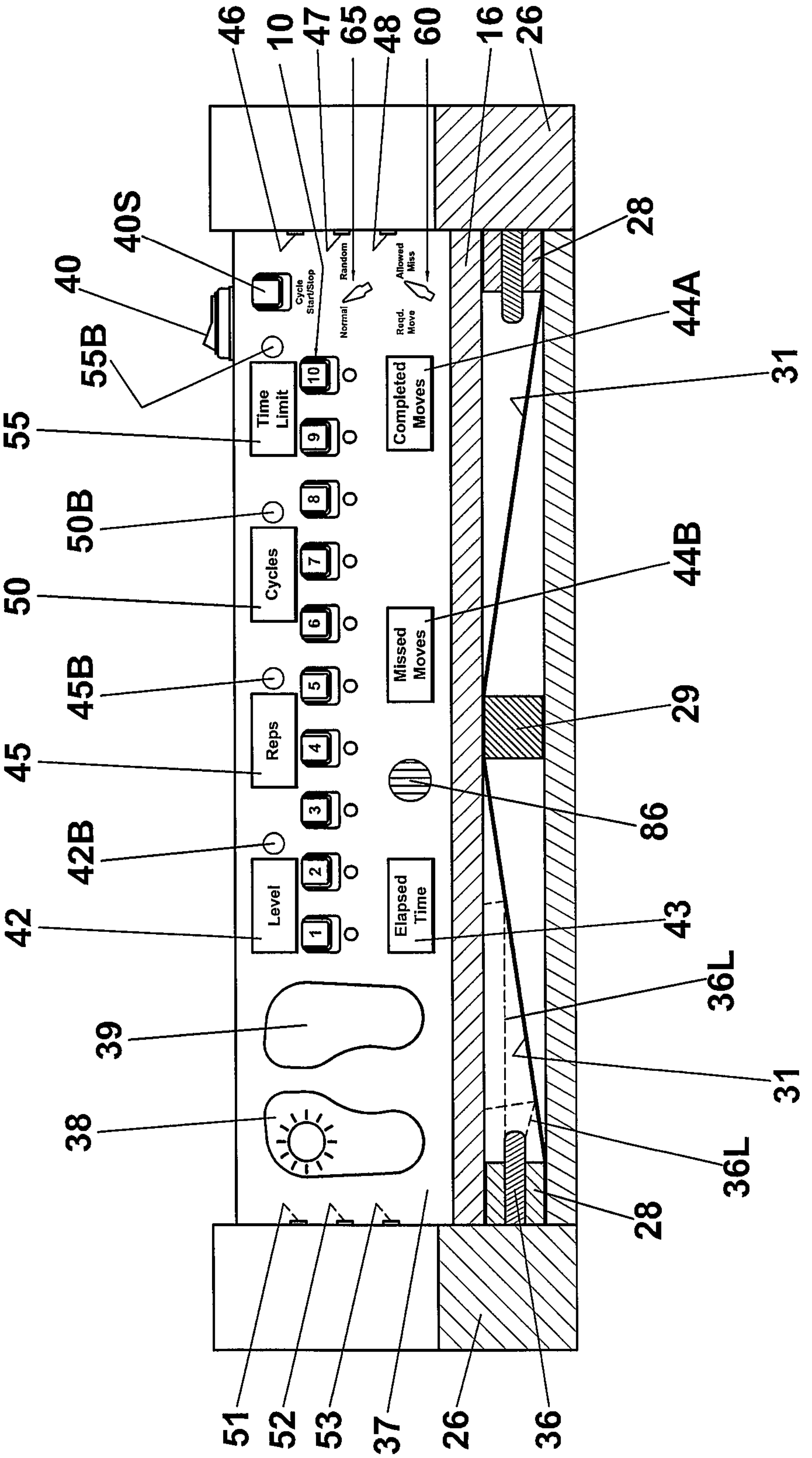
FIG. 5 is an enlarged section taken through FIG. 4 at line 5-5 and viewed in the direction of the arrows.

Referring now in particular to FIGS. 2 and 5 and, as mentioned above, the control housing 24 has the front panel 23. It also has a rear panel 37 facing toward the rear portion of the machine. It has switch selectors and displays on it. Panel 37 has two foot-image display sites representing the left foot at site 38 and the right foot at site 39. An ON/OFF switch 40 is provided above the panel. The panel has ten exercise-specifying selector buttons in a row 10. Each of the exercises is different from the others and it is intended that the platform and footprint display illumination and visible and audible monitors to be described herein below, instruct the patient when and with which exercise to proceed. Each of the buttons may have a number on it or below it from 1-10, for example. Also, each has an indicator light under it to show when it has selected the related exercise for a therapy session. Each button may be used to operate a bi-stable switch of some type such that actuating the button once will close the switch, and activating the button again will open the switch. Switches responsive to button touch actuation may be used, but it is believed that switch response to button motion is preferable. In any case, illumination of a light under or in the button will alert the therapist to the condition of the switch. A program START/STOP switch 40S enables the therapist to start a therapy session program running, and stop it at any time desired, or permit the program to continue running until it automatically expires. A display 42 is provided to show the level (indicated by a level number) selected by the therapist and to which the patient should raise a toe or a heel during an exercise. Another display 43 is provided to show the elapsed time during a therapy session. A display 44A shows the number of specified moves made during an elapsed time interval. Display 44B shows the number of moves missed during an elapsed time interval. Display 45 shows the number of repetitions of each exercise that is to be made in one cycle of machine operation. Display 50 shows the number of cycles through the set of selected exercises are to be completed in a therapy session. Display 55 shows a time limit setting for the patient to successfully perform an exercise the number of repetitions requested, until the program controller advances to the next prescribed exercise.

Rotary switch knob 60 has a designated left-hand position requiring that each exercise move specified according to the above mentioned selections must be successfully performed before the machine advances from one exercise to another in a cycle. The right-hand position of the switch knob 60 permits move-attempts to fail and permits moves from one attempt to another and causes the display 44B to show missed or unsuccessful moves during a cycle. Rotary switch knob 65 has a left-hand position causing the sequence of exercise instructions to be the same in each successive cycle of exercises in a therapy session. A right-hand position of switch knob causes random sequence of exercise instructions from one cycle to the next.

A push button is shown adjacent each of the four displays 42, 45, 50 and 55. For a given selection, the associated button can be pushed repetitively by the therapist until the number shown in the display advances to what the therapist wants to program for the therapy session.

Figure 6:
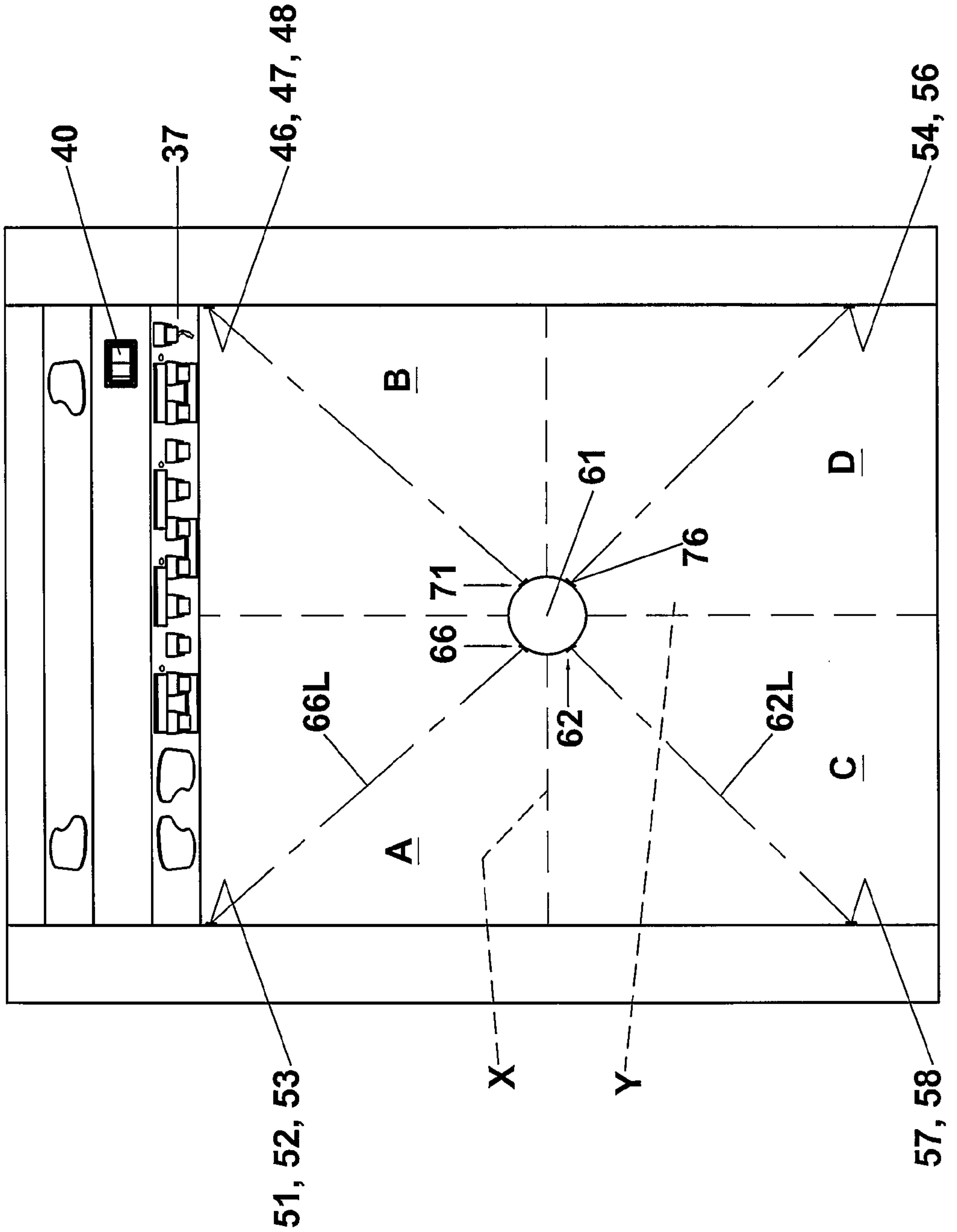
FIG. 6 is a top plan view of the machine showing the light radiation from the central light post or light stand to the light beam sensors on the inside faces of the machine.
Figure 7:
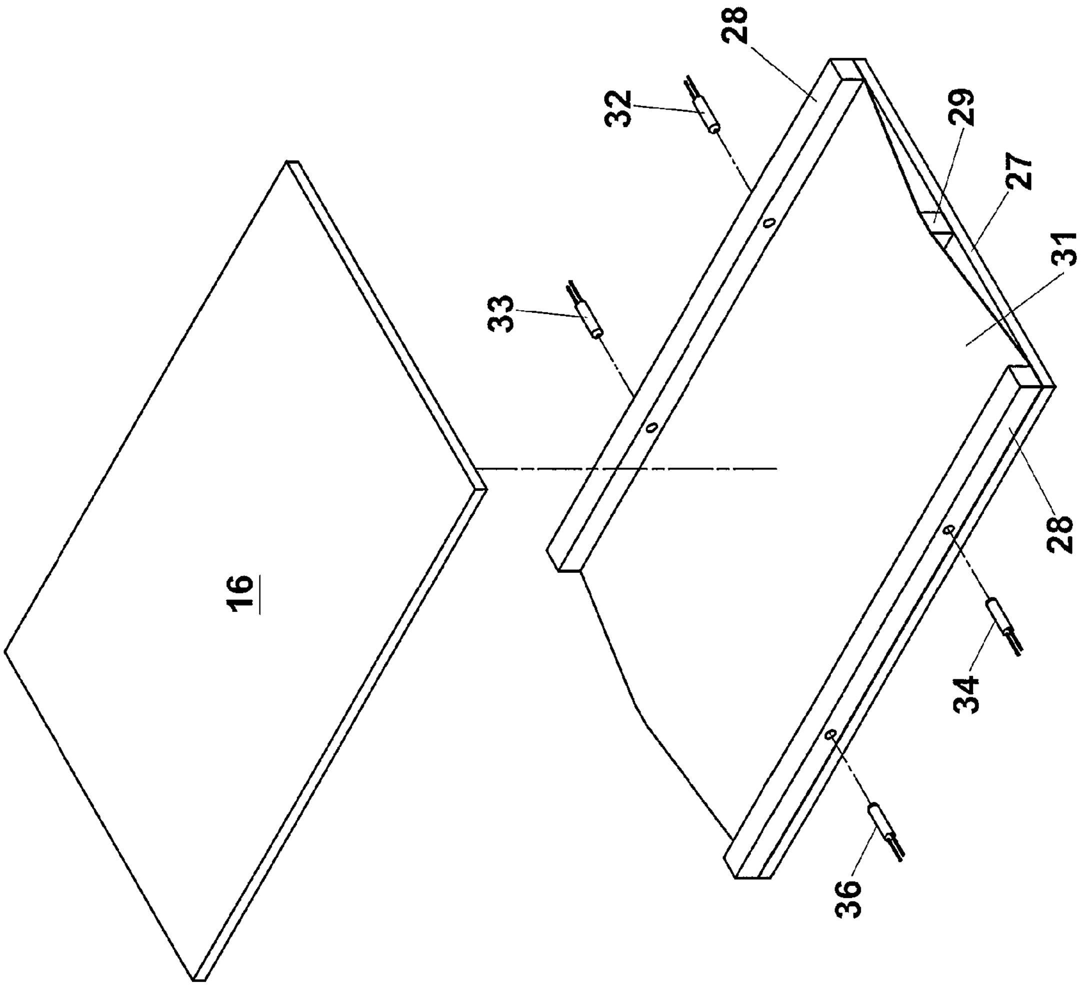
FIG. 7 is an exploded view of a platform underlighting a portion of the machine.
Figure 8:
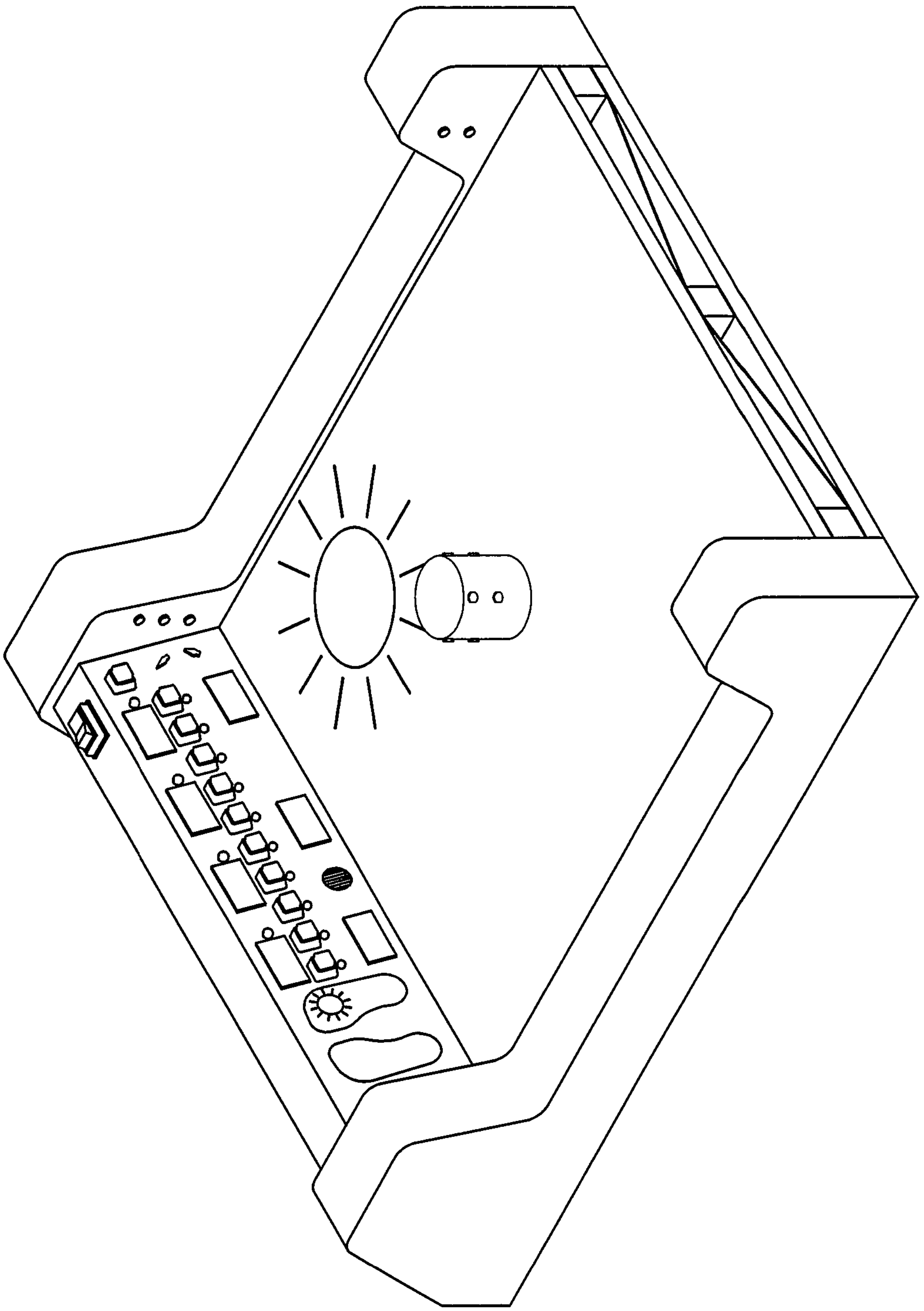
FIG. 8 is a perspective view of the machine displaying by platform underlighting, an instruction to the patient to lift a right toe.
Figure 9:
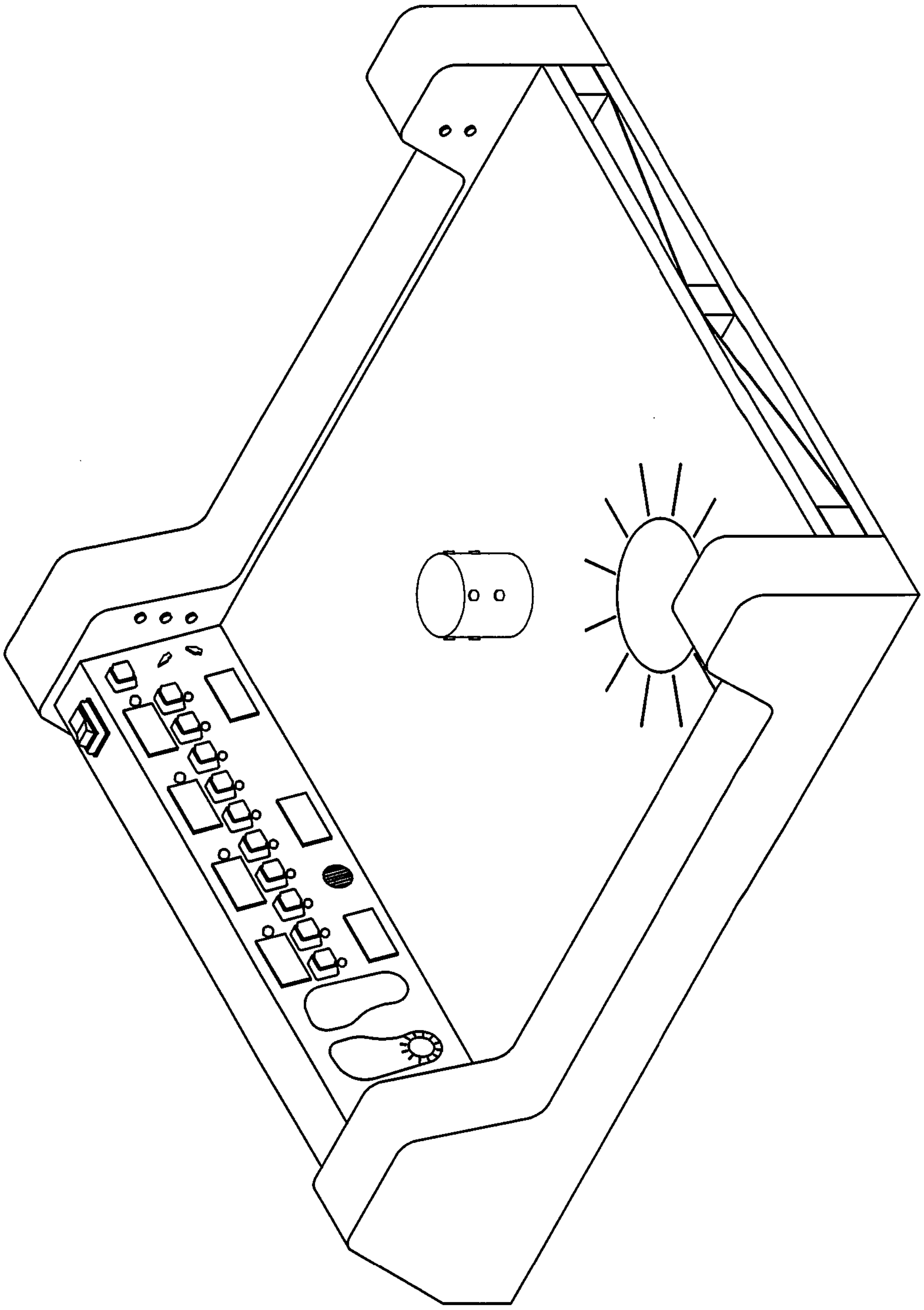
FIG. 9 is a perspective view of the machine displaying by platform underlighting, an instruction to the patient to lift a left heel.
Figure 10:
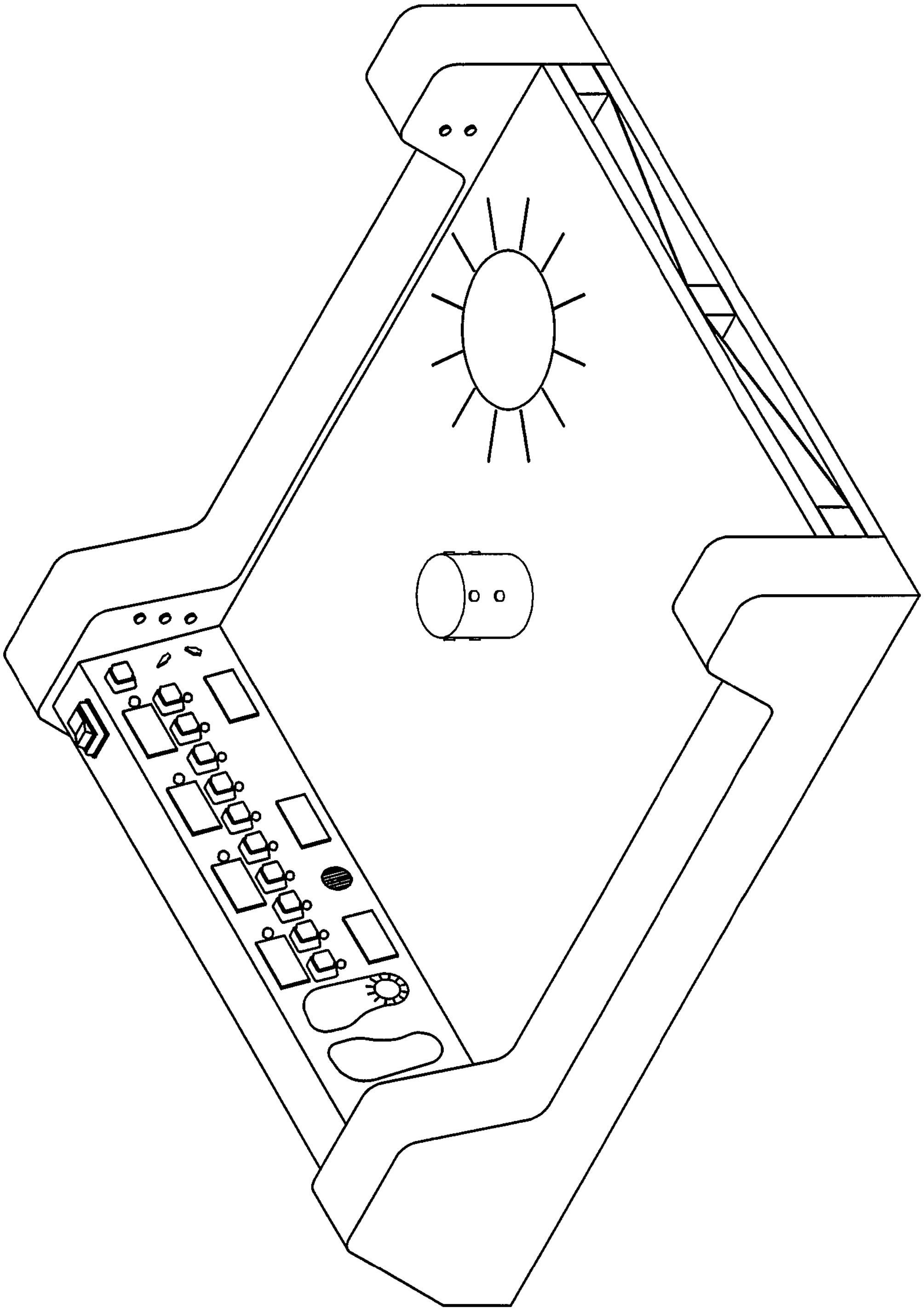
FIG. 10 is a perspective view of the machine displaying by platform underlighting, an instruction to the patient to lift a right heel.
Figure 11:
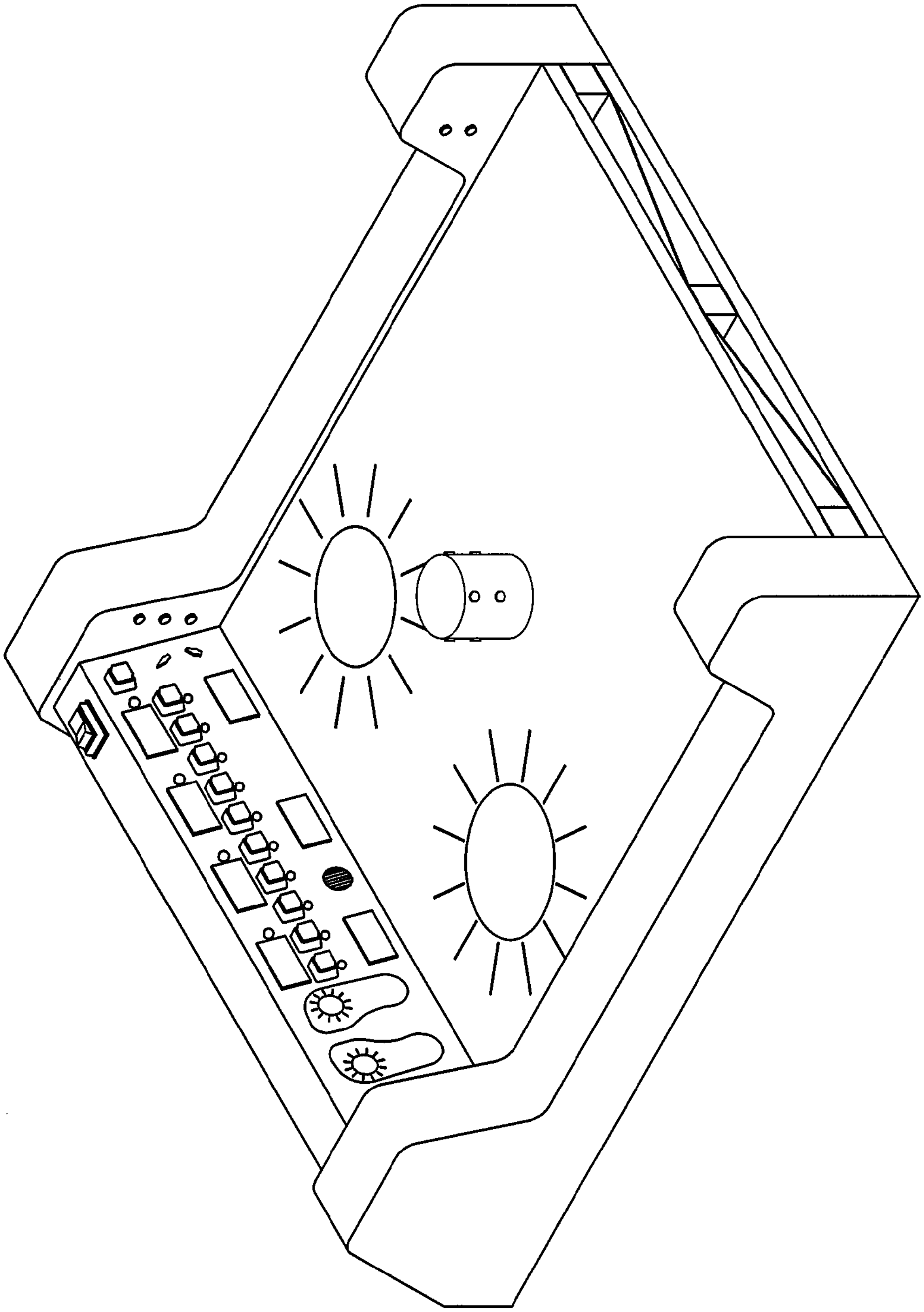
FIG. 11 is a perspective view of the machine displaying by platform underlighting, an instruction to the patient to lift a left toe and right toe.
Figure 12:
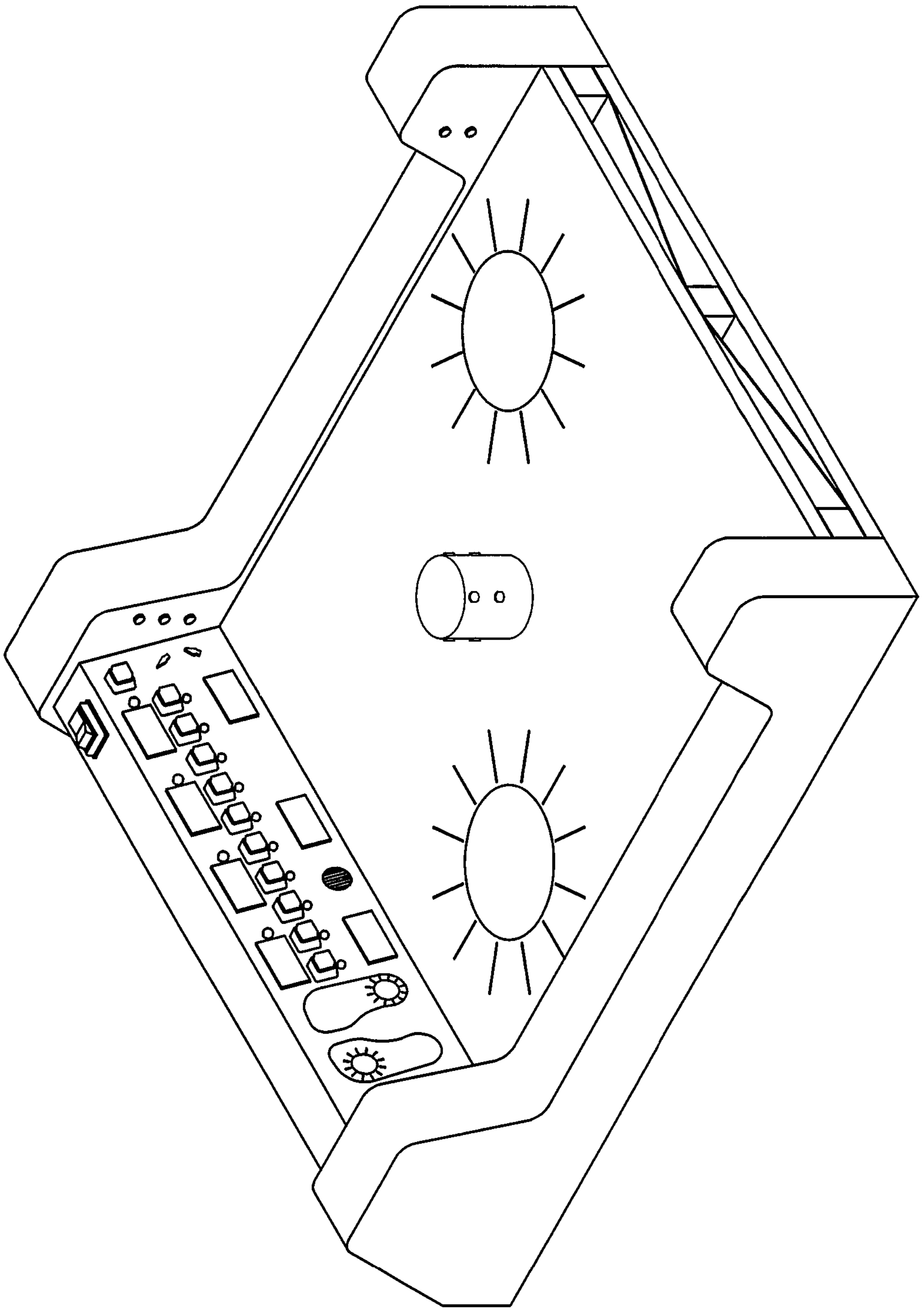
FIG. 12 is a perspective view of the machine displaying by platform underlighting, an instruction to the patient to lift a left toe and right heel.
Figure 13:
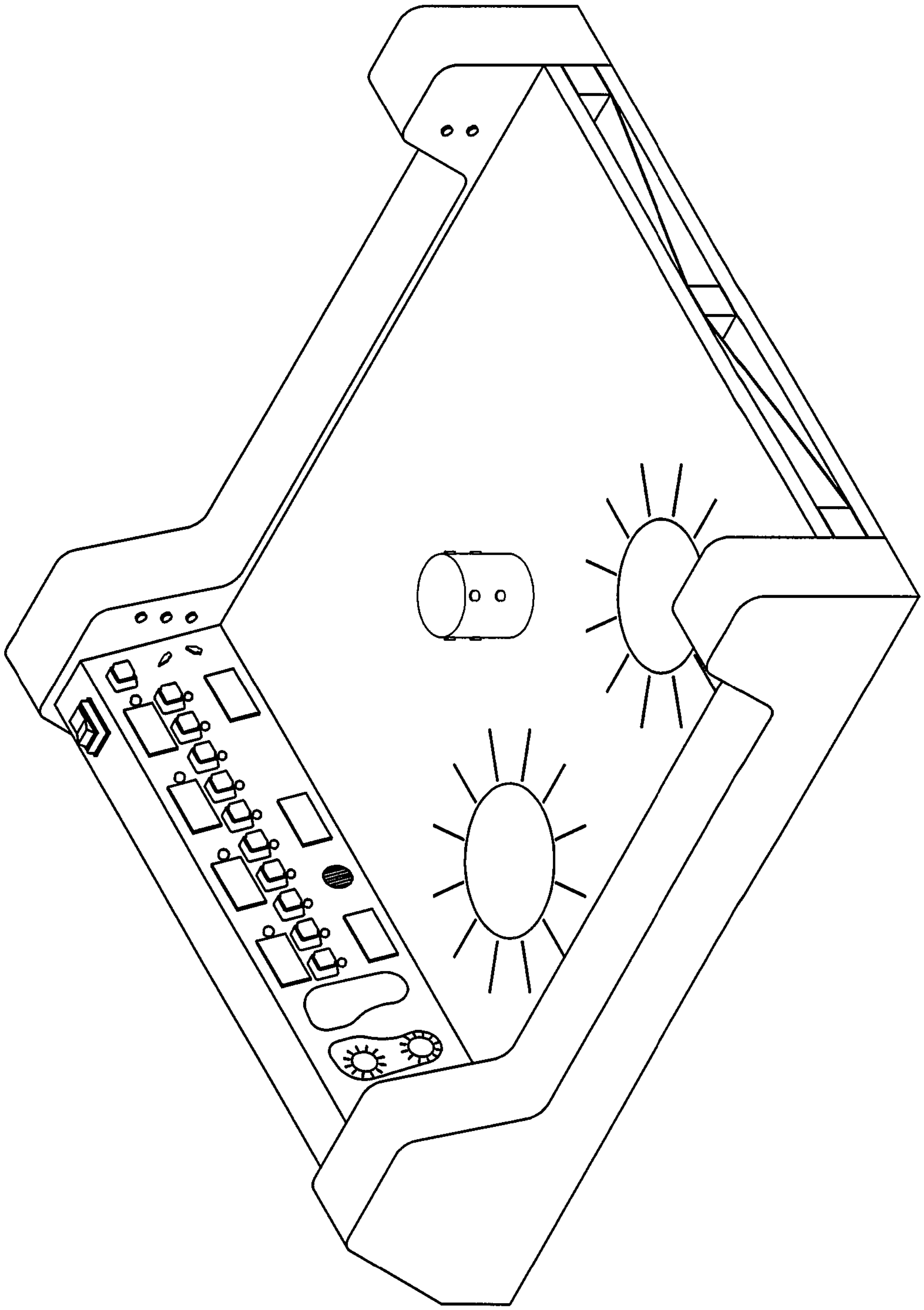
FIG. 13 is a perspective view of the machine displaying by platform underlighting, an instruction to the patient to lift a left toe and left heel.
Figure 14:
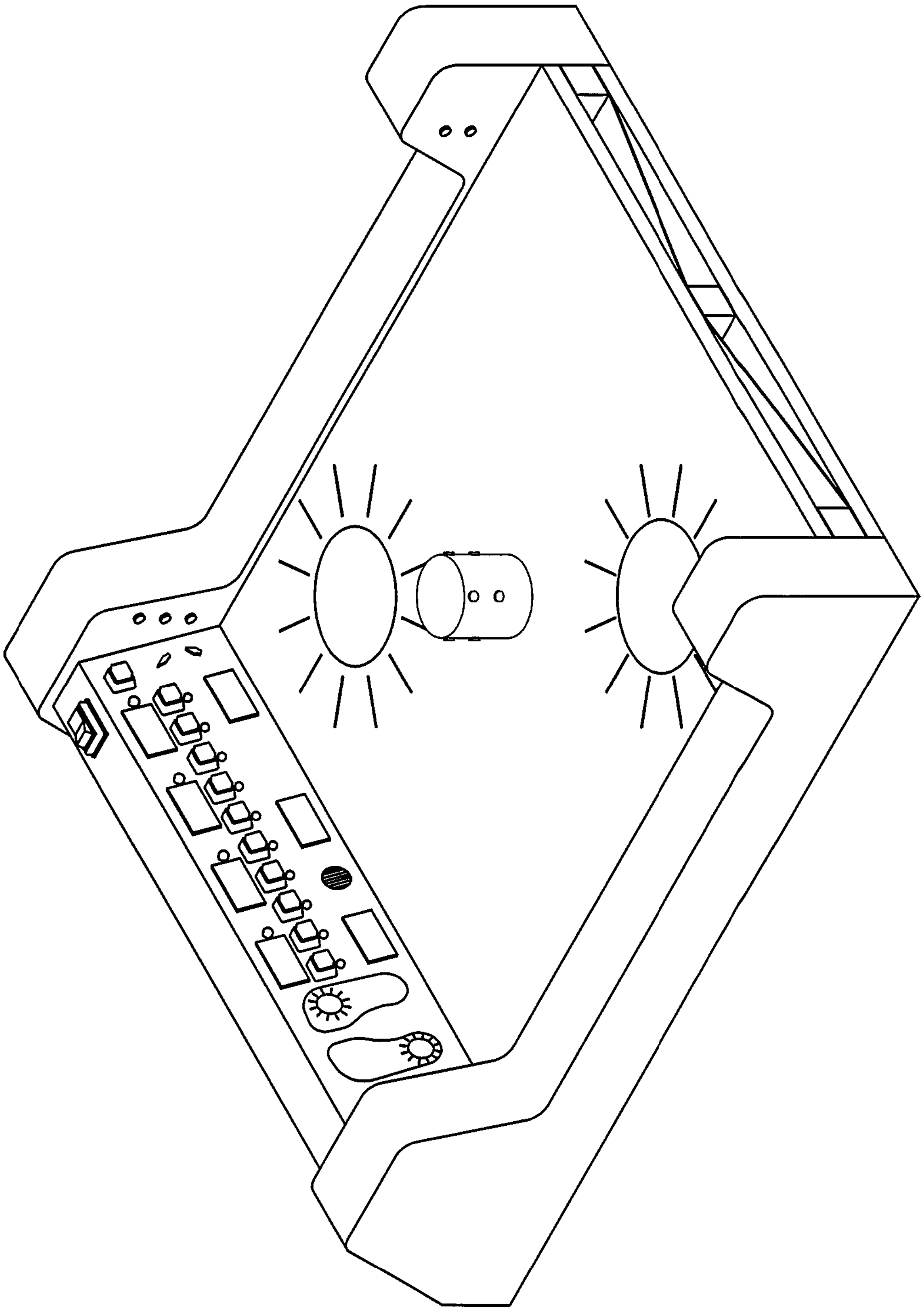
FIG. 14 is a perspective view of the machine displaying by platform underlighting, an instruction to the patient to lift a right toe and left heel.
Figure 15:
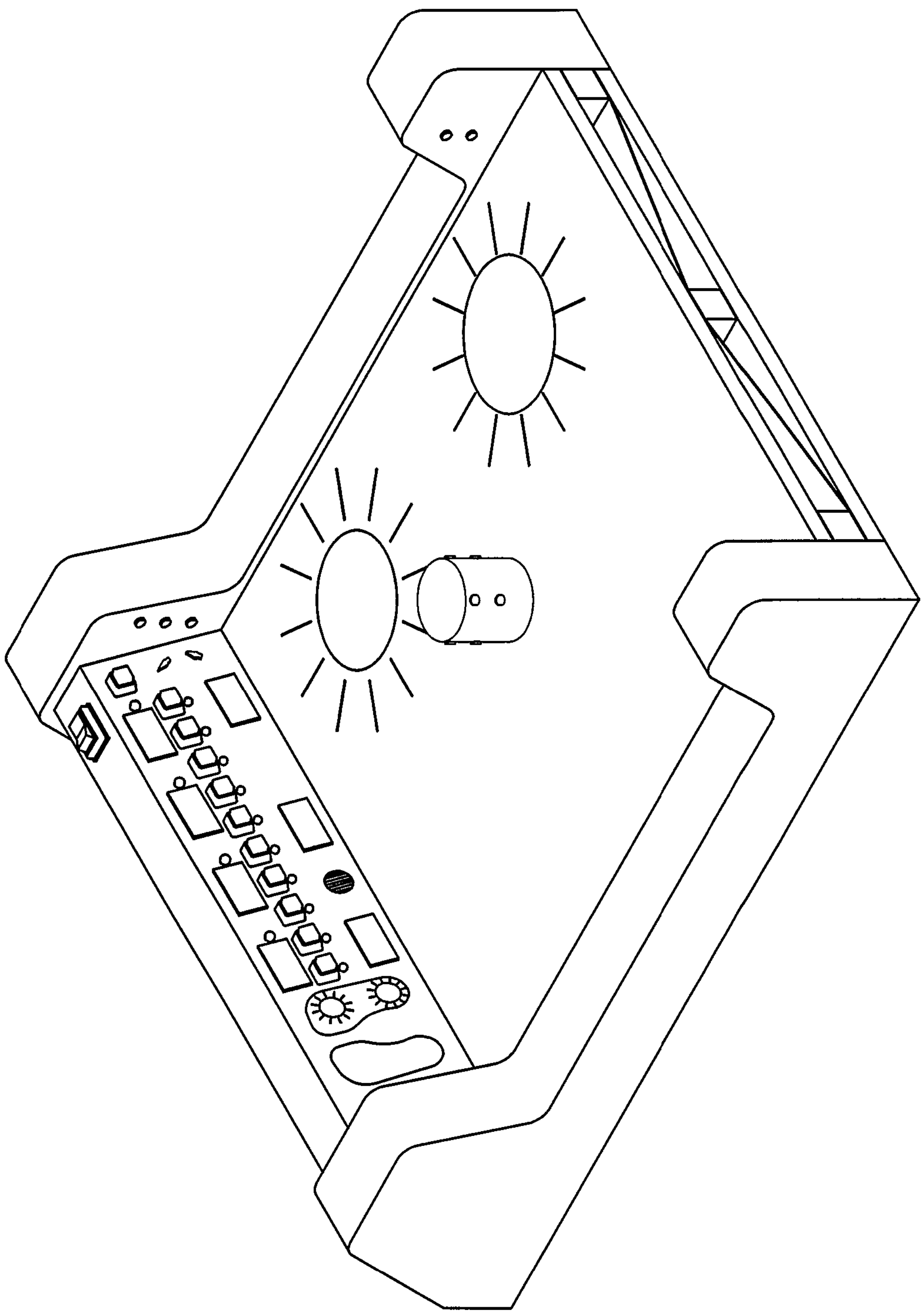
FIG. 15 is a perspective view of the machine displaying by platform underlighting, an instruction to the patient to lift a right toe and right heel.
Figure 16:
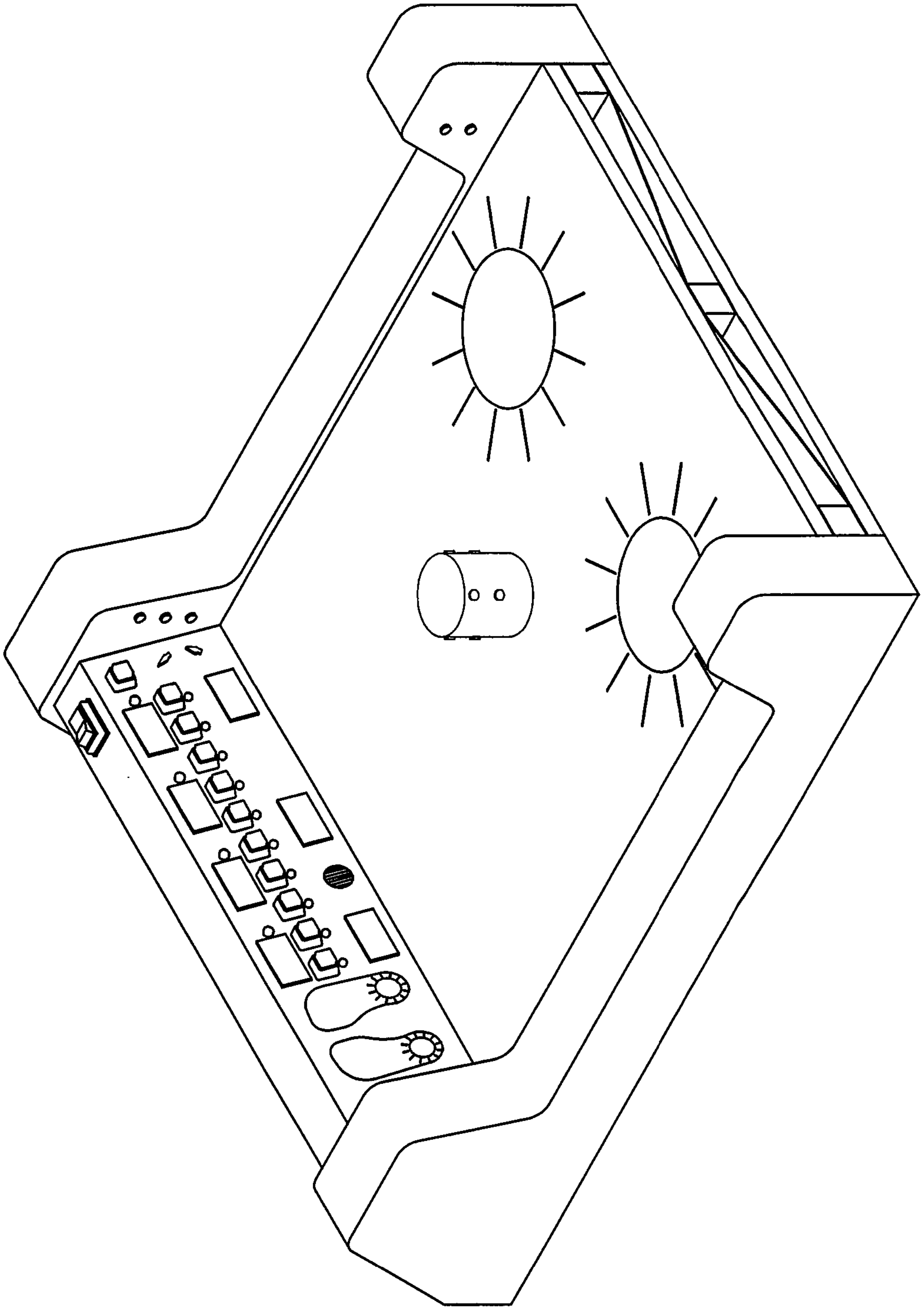
FIG. 16 is a perspective view of the machine displaying by platform underlighting, an instruction to the patient to lift a left heel and right heel.
Figure 17:
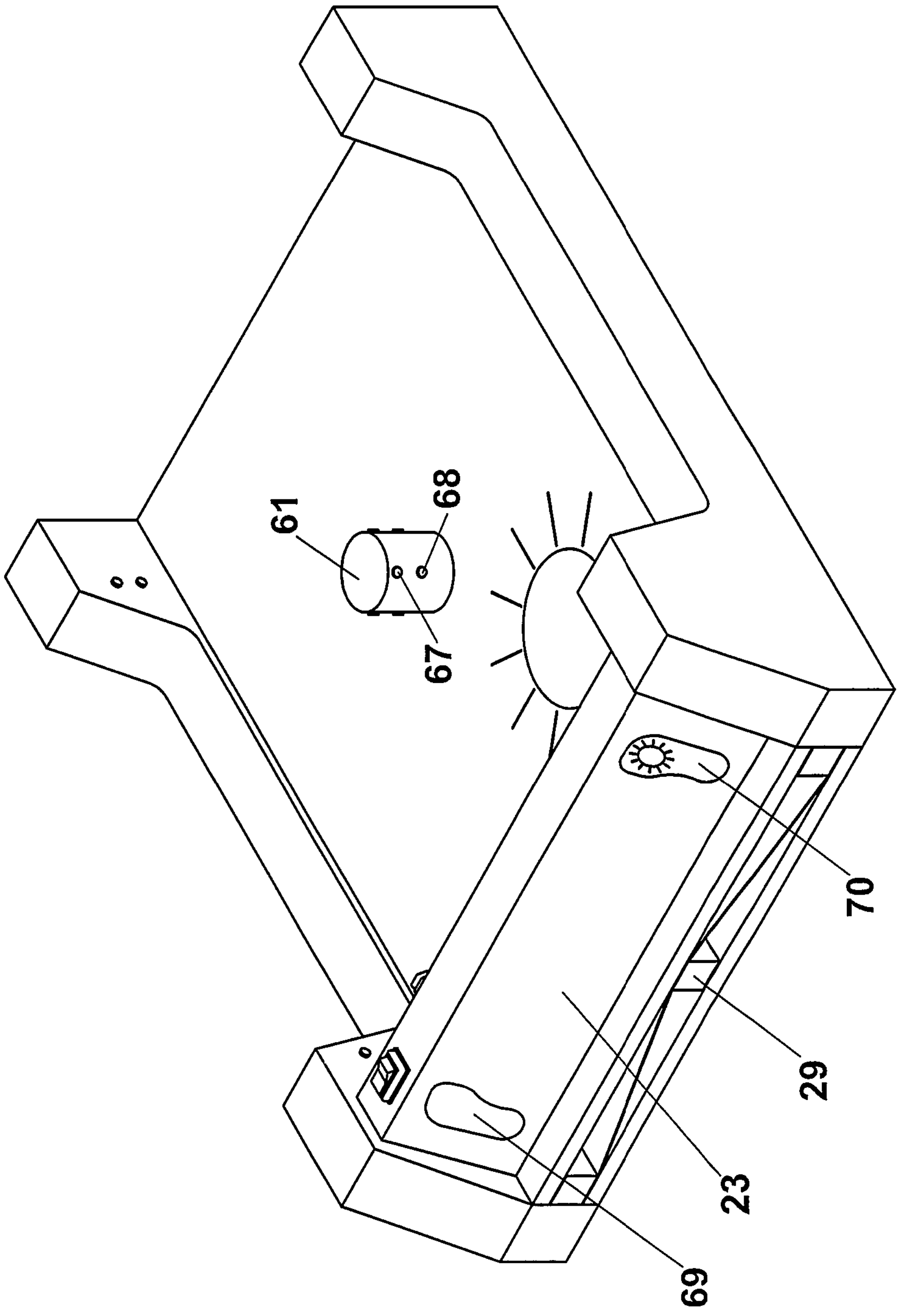
FIG. 17 is a perspective view of the front of the machine showing the two display sites for the foot images to be viewed in the mirror by the patient.

Referring now to FIGS. 2, 5 and 6, FIGS. 2 and 5 show three light sensors 46, 47 and 48 in the inside face of the right wall 26. The same arrangement is shown in FIG. 5 on the inside face of the opposite (left) wall 26 with sensors 51, 52 and 53. Similarly, the inside face of wall 26 at the right rear portion of the machine 11 has two light sensors 54 and 56, and the inside face of the left wall 26 at the rear portion of the machine has sensors 57 and 58.

Referring further to FIGS. 2 and 6, a light stand 61 is mounted in the center of the platform 16. It has four columns of lights. The lights in each column are directed at a different one of the four columns of light sensors as shown in FIG. 6. Considering, for example, that the space above and below platform 16 is in quadrants A, B, C and D with respect to the center of the light stand 61, and the quadrants are defined by imaginary vertical planes X and Y, the light beams from the column lights bisect the quadrants above the platform. For example, column 62 has two lights 63 and 64 directed, respectively, to sensors 57 and 58. Column 66 has lights 67 and 68 directed to sensors 52 and 53 (FIG. 5). The beams are represented by the dashed lines 62L for column 62, and lines 66L for column 66. Similarly, there are light columns 71 and 76 in the stand 61 and which direct beams to the sensors 46, 47 and 48 from column 71 and to sensors 54 and 56 from column 76.

It is believed that each of the eight lights in the light stand can be a light-emitting diode (LED). Each of the top four lights is directed toward the upper two sensors on the inside face of the machine front portion side wall to which the light is directed. For example, light 67 is directed to the sensors 51 and 52. The lower light in a column is directed to the lower sensor. For example, light 68 is directed to sensor 53. Other lighting devices might be useful for this purpose.

The above-mentioned front panel 23 has display sites 70 and 69 representing footprints like those at sites 38 and 39 on panel 37 so the patient looking at the mirror 19 will see footprint representations like what is seen from behind the machine as viewed by the therapist 18 behind the patient.

Operation

Referring now to FIG. 5, as mentioned above, each of the ten buttons in row 10 on the panel 37 has a number on it. These numbers refer to the various exercise movements which may be specified for the patient to make and are identified above with reference to the various figures of drawings. They will be repeated here for convenience.

| FIG. No. | Button No. | Activity |
|---|---|---|
| 3 | 1 | Lift left toe |
| 8 | 2 | Lift right toe |
| 9 | 3 | Lift left heel |
| 10 | 4 | Lift right heel |
| 11 | 5 | Lift left toe and right toe |
| 12 | 6 | Lift left toe and right heel |
| 13 | 7 | Lift left toe and left heel (entire left foot) |
| 14 | 8 | Lift right toe and left heel |
| 15 | 9 | Lift right toe and right heel (entire right foot) |
| 16 | 10 | Lift left heel and right heel |

The therapist will program the machine for a therapy session by selecting buttons for activating only the switches designated for the exercises which the therapist wants the patient to do during a therapy session. The therapist can use the button 45B associated with the repetition display 45 to establish the number of repetitions of that exercise to be performed. For example, if only buttons 1, 2 and 5 of row 10 are selected, and four repetitions are specified by the button 45B, the machine will cycle through these three exercises from one set of the prescribed four repetitions of exercise No. 1 to the next set of four repetitions of the exercise No. 2 and then to the set of the exercise No. 5. It can do this in the same sequence every time or it can be programmed by selector knob 65 to run these three exercises in a random pattern.

Figure 3:
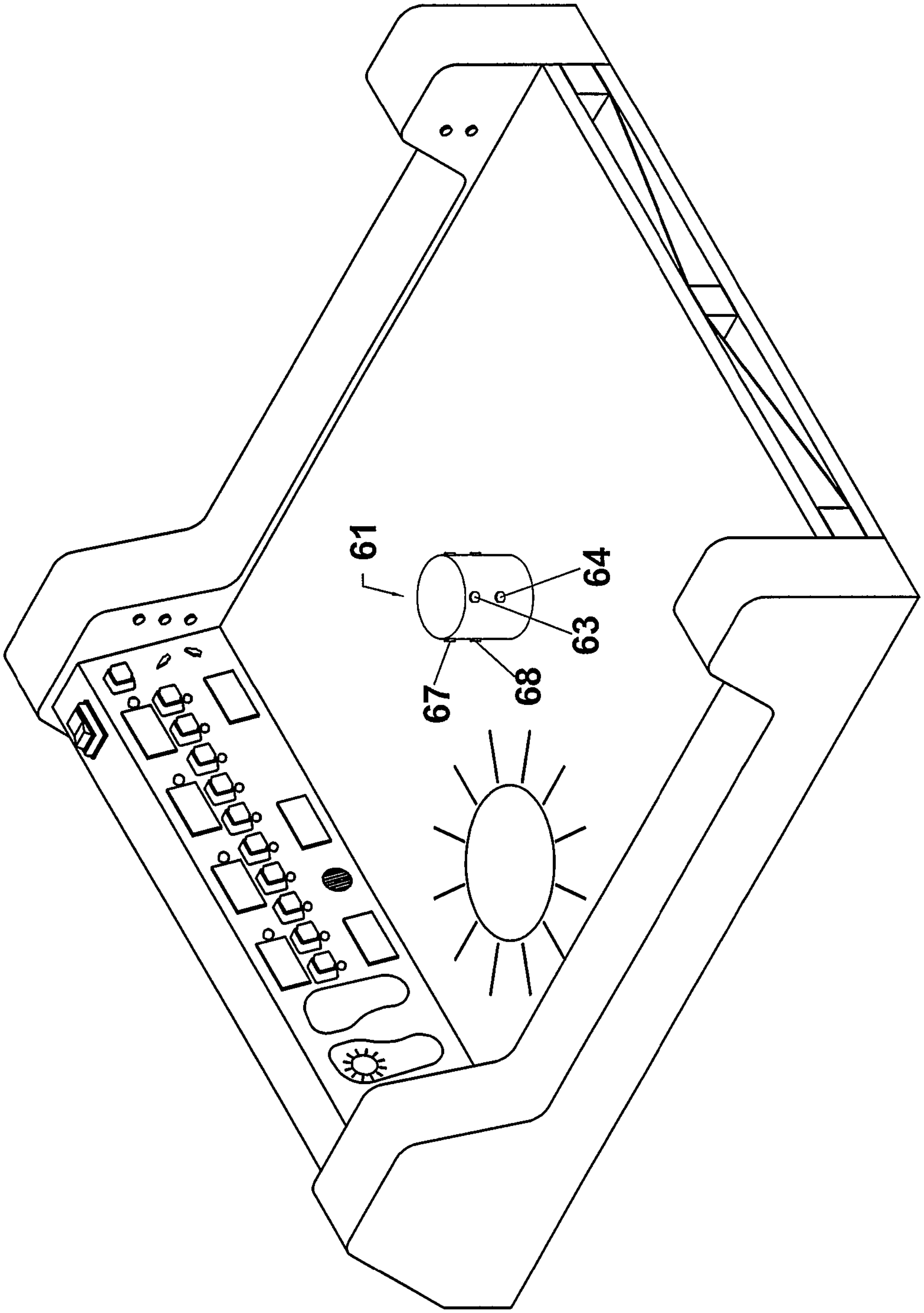
FIG. 3 is a perspective view of the machine turned on and programmed to show an instruction to the patient using the machine to lift the toe portion of the left foot.
Figure 4:
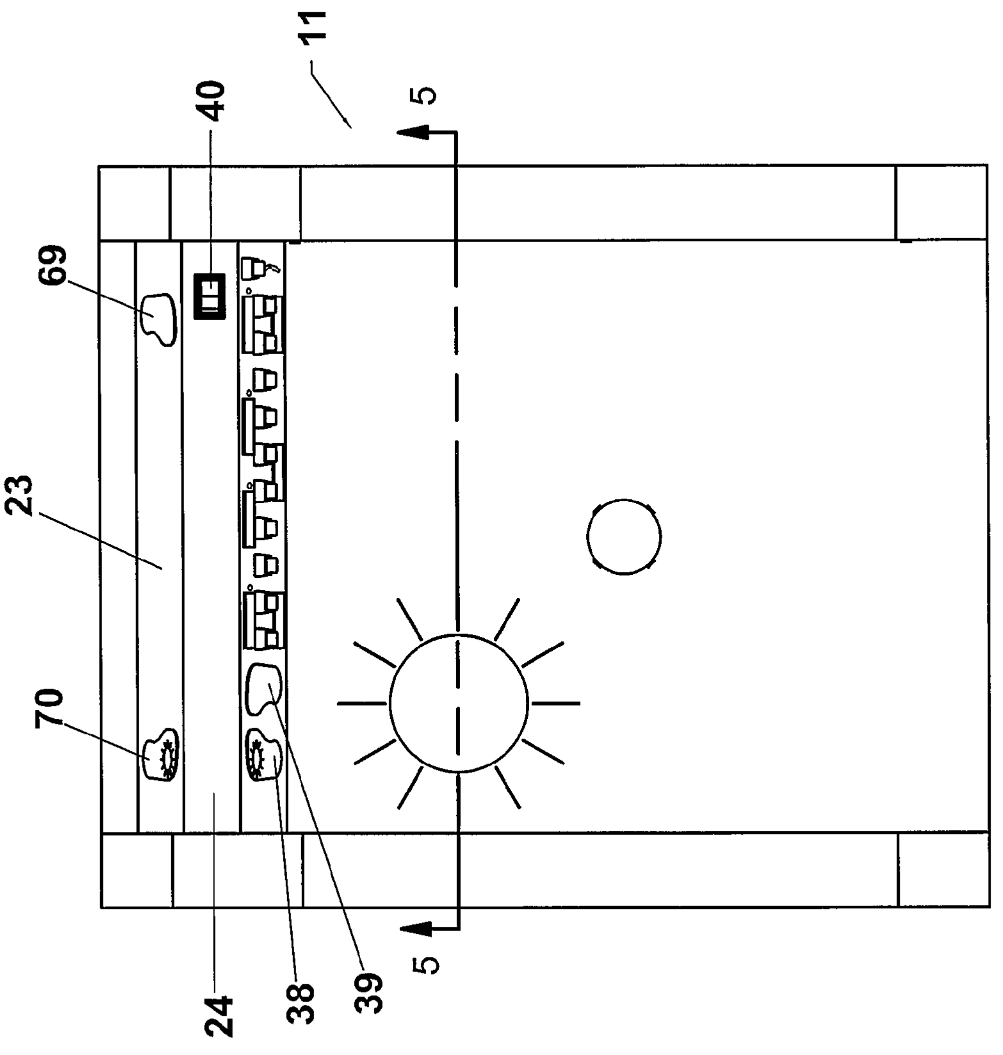
FIG. 4 is a top plan view of the machine with the FIG. 3 instruction.

An example of operation according to one of the available options is as follows: When the therapy session for the patient on the machine has been programmed by the therapist and the cycle has been started by operating switch 40S, the instruction (command) to perform the first exercise selected will appear. Let us say that is exercise 1 (lift left toe). A platform lighting source under quadrant A of platform 16 will turn on and illuminate the sunburst pattern on the platform as shown in FIGS. 3 and 4. The sunburst pattern or any other pattern desired can be provided for by suitable masking of the underside of the platform 16. If it is found that there is leakage of light above the reflector panel 31 and under the platform 16, from one quadrant to another, partitions can be provided under the platform on plane X, isolating space in quadrant A from quadrant C, and quadrant B from quadrant D. Isolation along plane Y between quadrant A and quadrant B, and between quadrant C and quadrant D is already provided by the crown in panel 31 at the support 29. When the platform lighting source is turned on, a light will also be turned on and appear through the toe portion of the left foot diagram 38 on the control housing panel 37. Additionally, a light will appear on the toe portion of the left foot diagram 70 on the panel 23 of the control housing and can be seen in the mirror 19 by the patient standing erect without bending over or otherwise looking down. The height of the mirror position can be adjusted and the mirror can be tilted to adapt the machine to the stature of the patient. So the patient can exercise and get instruction from the machine while looking straight ahead. The therapist looking on will be able to see the machine's commands by looking at the lights in the platform 16 on which the patient is standing or on the panel 37. Once the first command is displayed by means of the light in the floor and on the control panel and in the mirror, that command will remain until the patient performs the required movement, i.e., lifts the toe portion of his or her left foot by an amount equal to the level of one of three sensor heights selected by the therapist with button 42S during programming. The upper light or lower light in the light stand column directed to the selected sensor will be turned on. For example, for the left toe, it will be light 67 directed to sensor 51. When the patient lifts the left toe of a slipper or shoe enough to allow the beam 67 to reach sensor 51, that sensor responds to count a completed move. Thus, after the sufficient amount of lift specified by the therapist is detected by the machine, and the number of repetitions of successful lifts prescribed by the therapist have been counted, the machine cycles on and displays the instruction to proceed with the next exercise specified. The score is kept by timing the length of time (display 43) it takes for the patient to finish the program.

A second option in the program is to allow the patient a prescribed length of time set by button 55B to perform a given exercise and, if that exercise is not performed correctly in the time allowed, the machine goes on to the next exercise instruction. In this method of operation, the score is kept both by time required to finish the program and number of exercises or repetitions missed shown in display 44B. In this mode, the therapist can have a record of the exercises that are more difficult for the patient to perform.

A third option in the program relates to the sequence of commands given to the patient. This sequence can be the same every time the program is run or it can be random as desired by the therapist. This is selected by a simple program setting as by knob 65 on panel 37, for example, as mentioned above.

The therapist can use the same program for a given patient for several days and, thereby, give the patient a goal of beating the previous day's performance on the given program.

Figure 18:
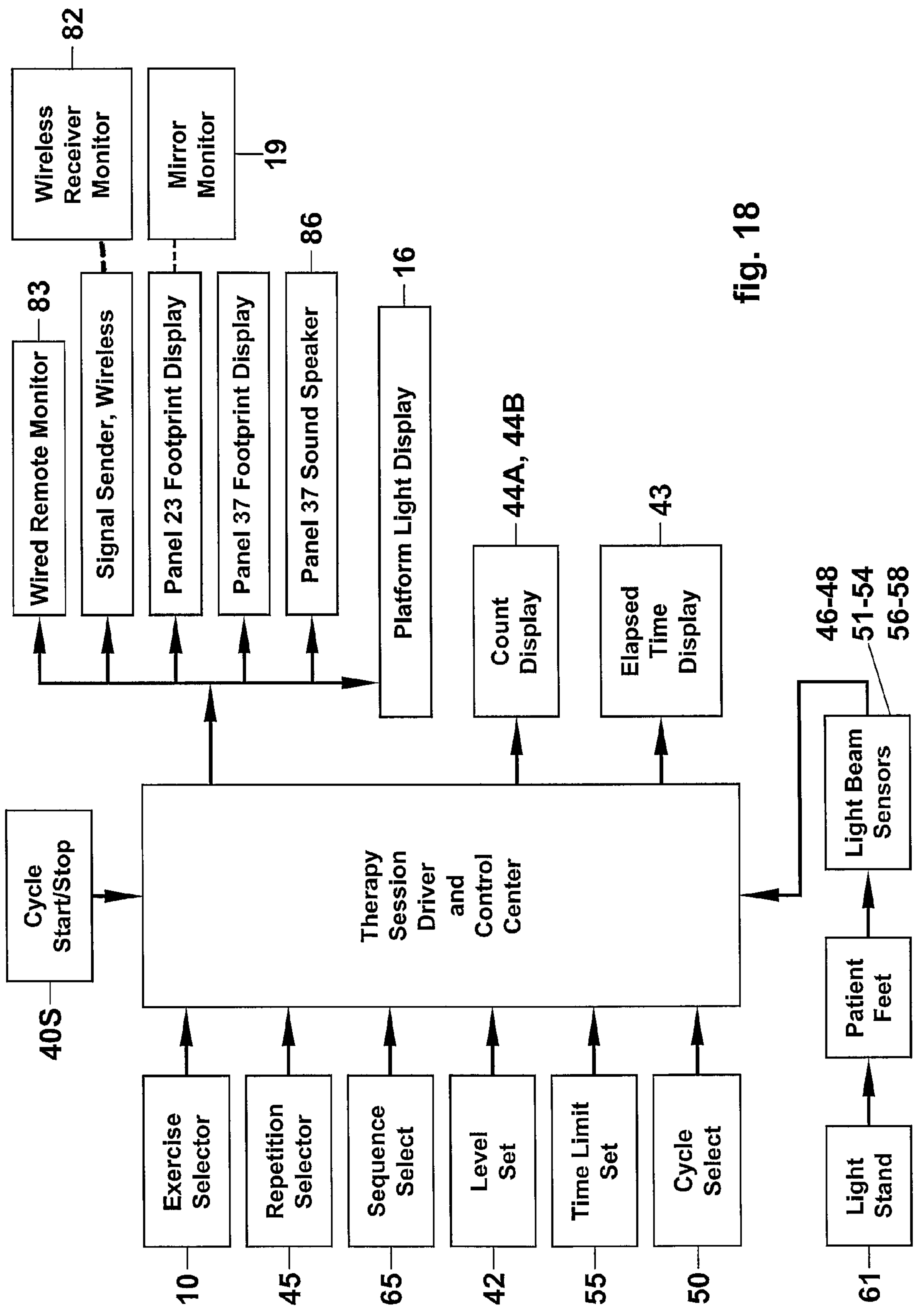
FIG. 18 is a general block diagram for example of relationships of functional components of the apparatus.

Referring to FIG. 18, alternative or supplemental monitor arrangements are provided. In this example, a wireless signal sender 81 receives an input from the control center and produces an audio-visual output to the wireless receiver 82, which may be located on the post 21 or wherever else it will be of use to the patient. The information transmitted to it is the same instruction as is provided by the therapy program entered by the therapist. This approach can be beneficial particularly in an installation of a portable apparatus where location or mounting of a mirror could present challenges. Also, it provides not only the opportunity to use the video approach, but also an audible component of beeps or tones or using voice-simulated instructions to aid the patient whose sight is poor or lost. This also provides an option for the patient, depending on the condition of the patient, to do prescribed therapy without full-time presence and attention of the therapist. This wireless approach may use electronic radio frequency, optical, sonic or ultra-sonic devices. A simple sonic approach for the patient can be employed using a sounder 86 in the control housing or elsewhere in the machine 11, producing a set of beeps or other sounds alerting the patient when progression, for example, from exercise No. 1 to exercise No. 2 is to begin. Another possibility is to provide an audible or visible or combined, annunciator 83 remote from but wired to the controller, for flexibility of the relative locations of the controller where the patient is standing, and the annunciator.

With the foregoing information, the circuitry and software to provide the functionality described, is well within the skill of art, and may be implemented according to the preferences of those involved. Also, useful substitutions for materials specifically mentioned above, can be readily found and used and remain within the scope of the invention as claimed herein below.

The invention claimed is:

1. Rehabilitation therapy apparatus comprising:

platform for support of a human therapy patient while standing;

a plurality of platform lighting sources for illuminating portions of said platform in four quadrants around a center, said platform having areas in said portions which are made of material capable of transmitting light from said sources through said areas for viewing from above said platform, to provide instructions to perform exercises;

a control housing associated with one end of the platform, the control housing comprising a front face and a rear face on opposite sides of the control housing from one another, with the rear face facing the human therapy patient when standing on the platform;

a monitor disposed above the control housing and positioned to show the front face of the control housing to the human therapy patient when standing erect on the platform;

an exercise instruction program driver; and an exercise selector having a plurality of selector switches associated with said platform and said driver and operable, when set, to enable said driver to activate said platform lighting sources sequence in accord with settings of said selector switches, to thereby illuminate those of said areas of said platform specified for selected exercises in a sequence of exercises, wherein the exercise instruction program driver is configured to provide instructions for performance of selected exercises by the human therapy patient.

2. The apparatus of claim 1 and further comprising:

an audio device coupled to said driver and positioned to enable a patient to hear an exercise instruction signal.

3. The apparatus of claim 1 and further comprising:

a monitor coupled to said driver and positionable relative to said platform to be viewed by a patient standing erect on said platform to view the monitor.

4. The apparatus of claim 3 and wherein:

the monitor is a mirror.

5. The apparatus of claim 3 and wherein:

said monitor is a wireless signal receiver.

6. The apparatus of claim 5 and further comprising:

a wireless signal sending device coupled to said driver; and wherein said monitor is coupled to said driver through said sending device; and said monitor is movable by the patient while using the apparatus for viewing a display concurrently with area illumination on said platform.

7. The apparatus of claim 1 and wherein:

said lighting sources are at a level lower than the platform, for illuminating said platform from under said platform, said apparatus further comprising:

a machine containing said platform and said lighting sources and having a front portion and a rear portion;

a control panel at said rear face of said control housing and which has a display of left and right foot representations; and a display panel at said front face of said control housing and which has a display of left and right foot representations, wherein the monitor comprises a mirror disposed above said front portion and positioned to reflect said display from said front face to a patient when standing erect on said platform.

8. The apparatus of claim 7 and wherein:

said mirror is adjustable vertically and is tiltable for adaptation to patients of different heights.

9. The apparatus of claim 1 and further comprising:

a light stand above said center and having first and second vertically spaced arrays of lights above said platform;

four lights in said first array, each light directing a light beam in a different one of four directions through space above said four quadrants of said platform;

four lights in said second array, each light in said second array directing a light beam in a different one of four directions through space further above said four quadrants of said platform than are the beams from said first array;

sets of light sensors adjacent said quadrants at levels above said platform, a first of said sets having three sensors located at three different levels above said platform, a second of said sets having three sensors located at three different levels above said platform, a third set having two sensors located at two different levels above said platform, and a fourth set having two sensors located at two different levels above said platform; and a counter coupled to said sensors and responsive to activation of sensors in response to light beams received from lights in said light stand, to change a count in said counter.

10. The apparatus of claim 9 and further comprising:

a patient foot exercise lift level selector and indicator coupled to said exercise selector to activate a light in one of said arrays to provide a beam over a quadrant where a foot portion is to be exercised, to a light beam sensor, for selection of the level of the light beam available to a sensor upon lifting said foot portion to said level to change the count in said counter.

11. The apparatus of claim 10 coupled to said driver and further comprising:

a required successful move selector coupled to said driver and to said counter and operable, when activated, to prevent said driver from advancing from display of one selected exercise instruction to the next selected exercise instruction.

12. The apparatus of claim 9 and further comprising:

a repetition selector coupled to said exercise selector and operable to maintain an exercise instruction prescribed by said exercise selectors, during a selected number of repetitions of the exercise, before advance of said driver from one selected exercise instruction to the next selected exercise instruction in a sequence of instructions for selected exercises.

13. The apparatus of claim 12 and further comprising:

a cycle selector coupled to said driver and operable to cause said driver to repeat said sequence of said selected exercise instructions a desired number of times.

14. The apparatus of claim 12 and further comprising:

a sequence control selector coupled to said driver to enable choice between repetition of the same sequence of exercise instructions in repetitive cycles, and random presentation of said exercise instructions during successive cycles.

15. The apparatus of claim 9 coupled to said driver and further comprising:

a time limit selector coupled to said driver and to said counter to select a duration for presentation of a selected exercise instruction and cause said driver to advance to presentation of a next exercise instruction.

16. The apparatus of claim 9 and further comprising:

a machine containing said platform and having a front portion and a rear portion, and a control housing;

a control panel at a face of said control housing and which has a first display of left and right foot representations;

said machine having left and right side walls with:

said first set of three sensors located at said left side wall near said front portion;

said second set of said three sensors located at said right side wall near said front portion;

said third set of sensors located at said left side wall near said rear portion; and said fourth set of sensors located at said right side wall near said rear portion.

17. The apparatus of claim 16 and further comprising:

a reflector panel under said platform;

a light reflecting surface on said reflector panel to receive light from said platform lighting sources and project light received from said sources through said areas for viewing from above said platform.

18. The apparatus of claim 17 and further comprising:

masking material on the bottom surface of said platform and arranged to provide a distinct pattern of said projected light in said platform.

19. The apparatus of claim 16 and further comprising:

operators on said control panel and coupled to said selector switches to operate said switches for selecting said instructions to perform exercises during a therapy session.

20. The apparatus of claim 19 and further comprising;

a cycle start/stop switch on said control housing.

21. An apparatus comprising:

platform configured to support a user of the apparatus;

a plurality of platform lighting sources for illuminating portions of the platform, the platform comprising material configured to transmit light for viewing from above the platform, wherein the platform lighting sources are configured to selectively illuminate and provide a visual cue for the user to perform a responsive action;

a controller associated with the lighting sources and configured to control illumination of the lighting sources;

a control housing associated with the platform, the control housing comprising a first panel and a second panel, wherein the first and second panels are configured to provide information relating to the visual cue; and a mirror associated with the apparatus such that one of the first panel and the second panel is visible to the user exclusively via the mirror when the user is standing erect on the platform.

22. The apparatus of claim 21, wherein the controller is contained within the control housing.

23. The apparatus of claim 21, wherein the control housing is associated with an edge of the platform, and the first panel is proximal with respect to the edge of the platform and the second panel distal with respect to the edge of the platform.

24. An apparatus comprising:

platform configured to support a user of the apparatus;

a light stand associated with the platform, the light stand comprising a plurality of lights and being configured such that the lights emit a beam of light extending above the platform;

a plurality of sensors associated with the platform and configured to detect the beam of light; and a controller associated with the light stand and the plurality of sensors, wherein the apparatus is configured such that when a user on the platform lifts at least a portion of a foot a predetermined distance above the platform, the sensors detect an absence of the light beam, and the controller records a number of instances in which absence of the light beam is detected.

25. The apparatus of claim 24, wherein each of the plurality of lights is associated with a predetermined distance above the platform.

26. The apparatus of claim 24, further comprising a plurality of lighting sources, wherein the lighting sources are configured to selectively illuminate and provide a visual cue for the user to perform a responsive action.

27. The apparatus of claim 1, wherein the plurality of selector switches are configured to permit selection of at least one of:

a number of repetitions of the selected exercises to be performed by the human therapy patient, a duration of time for performing the selected exercises, and a sequence of commands for performance of the selected exercises.

* * * * *